United States Patent [19]

Oscarsson

[11] Patent Number: 4,667,927
[45] Date of Patent: May 26, 1987

[54] LIQUID FLOW METERING DEVICE
[75] Inventor: Rolf A. Oscarsson, Hudson, Ohio
[73] Assignee: Rao Medical Devices, Inc., Hudson, Ohio
[21] Appl. No.: 806,543
[22] Filed: Dec. 9, 1985

Related U.S. Application Data

[63] Continuation-in-part of Ser. No. 796,316, Nov. 8, 1985.
[51] Int. Cl.⁴ ............... F16K 5/10; F16K 47/04
[52] U.S. Cl. .................... 251/209; 251/181; 251/297; 251/309; 251/904; 285/359; 285/423
[58] Field of Search ........... 251/209, 904, 297, 181, 251/309; 285/359, 423

[56] References Cited

U.S. PATENT DOCUMENTS

| | | | |
|---|---|---|---|
| 2,014,642 | 9/1935 | Andrews | 251/209 X |
| 2,067,346 | 1/1937 | Rovinsky | 251/209 X |
| 3,012,752 | 12/1961 | Buck | 251/904 X |
| 3,355,141 | 11/1967 | Cooper | 251/297 X |
| 3,484,077 | 12/1969 | Porter | 251/181 |
| 3,788,599 | 1/1974 | Cloyd | 251/904 X |
| 3,788,602 | 1/1974 | Kitzie | 251/904 X |
| 4,093,178 | 6/1978 | Hughes et al. | 251/297 X |
| 4,207,923 | 6/1980 | Giurtino | 251/181 X |
| 4,471,809 | 9/1984 | Thomsen et al. | 251/209 X |

Primary Examiner—Arnold Rosenthal
Attorney, Agent, or Firm—Body, Vickers & Daniels

[57] ABSTRACT

A device for metering the flow of a liquid medium passing therethrough comprises a plastic stem member having a cylindrical metering drum element projecting into and rotatively engaged in liquid tight relation with the cylindrical wall of a bore chamber in a body member to rotatively mount the stem member therein. A diametrically slotted headed stud projecting endwise from the drum element is contracted and inserted through a bore opening in the end wall of the chamber in the body member to cause the head end of the stud to snap-lock behind the chamber end wall and thus secure the stem and body members together in assembled rotative relation. Diametrically opposite arcuate metering slots of decreasing cross-sectional size in the cylindrical surface of the drum element and leading from opposite ends of a diametrical cross passageway in the drum, meter the flow rate of the liquid medium into and out of the chamber through diametrically opposite port openings in the chamber side wall, depending on the relative rotative position of the stem and body members. Generally radially outward extending actuating arm means on the stem and body members enable relative rotative movement thereof to a selected metering position.

29 Claims, 8 Drawing Figures

LIQUID FLOW METERING DEVICE

The present application is a continuation-in-part of my application Ser. No. 796,316, filed Nov. 8, 1985 entitled Liquid Flow Control Device.

This invention relates in general to a device for metering the flow of a liquid medium through a tubing system and, in particular, to an in-line light weight type of such device suitable for medical use such as in intravascular catheter systems.

BACKGROUND OF THE INVENTION

There are many instances where the flow of a liquid medium through relatively small diameter pliable plastic tubing systems is regulated by the incorporation in the tubing system of a flow control or metering device of comparatively small size and light in weight so that the device is capable of being supported or suspended in place in the tubing system solely by the tubing itself. In the medical field, for example, such type flow control or metering devices are commonly employed to regulate the flow of medical fluids through intravascular catheter systems which customarily employ elastically deformable or compressible plastic tubing such as that commercially known as Tygon tubing and which are conventionally used for various medical purposes such as, for example, blood dialysis, clinical monitoring of a patient's blood system, or infusion of various medical fluids into a patient's venous system.

The flow control or metering devices heretofore employed for such purposes generally have been of complicated construction difficult to fabricate and/or assemble. With such prior flow control or metering devices, moreover, and more particularly those employed for regulating the flow of medical fluids to a certain number of drops thereof per given time interval, the adjustment or setting of the device to the desired minimal flow rate for the medical fluid through the device generally has been a difficult and critical operation to perform involving in most cases an undesirable time consuming trial and error procedure.

The prior type metering devices, moreover, generally have not been provided with any visible indicator means or any so-called memory device affording a ready indication of the adjusted setting of the metering device that provided the desired flow rate of the liquid medium through the device. As a result, when such prior metering devices were moved to a closed position for some reason or other so as to close off the flow of the liquid medium through the tubing system, for instance, to check the reason for a stoppage of the liquid flow through the tubing system, it then became necessary to manually readjust the setting of the device, generally by trial and error procedure, in order to restore the previous setting of the device so as to provide the same rate of flow of the liquid medium through the tubing as before. Obviously, such a resetting procedure constitutes a time consuming operation and therefore an undesirable characteristic of the prior type fluid flow metering devices such as used for medical purposes.

SUMMARY OF THE INVENTION

The present invention contemplates a new and improved liquid flow metering device of the above described general type which overcomes all of the above referred to problems and others and provides a device of such type which is of simple and inexpensive construction having flow controlling members which are quickly and easily assembled in rotative relation to each other and having retaining means for maintaining the flow controlling members in a selected rotative metering position.

Briefly stated, in accordance with one aspect of the invention a liquid flow metering device of the general type referred to above is comprised of a stem member having a cylindrical metering drum projecting into and rotatively engaged in liquid tight relation with the cylindrical wall of a bore chamber in the body member and provided with a pair of diametrically opposite arcuate metering grooves of progressively decreasing cross-sectional size in the cylindrical drum surface for metering the flow rate of a liquid medium entering and leaving the chamber through diametrically opposite inlet and outlet port openings in the wall of the chamber.

In accordance with a further aspect of the invention, the molded plastic stem and body members are provided with outwardly extending actuating arm means for enabling the manual rotative movement thereof relative to one another, the actuating arm means on the stem member comprising a radially outward projecting lever arm and the actuating arm means on the body member comprising a radially outwardly extending sector-shaped frame having an arcuate outer bar portion centered on the turning axis of the stem and body members and across which the lever arm on the stem member extends in sliding pressure engagement therewith to provide a readily visible indication of the selected rotative metering position of the stem and body members.

In accordance with a still further aspect of the invention, the cylindrical drum element of the stem member projects into the chamber of the body member from an annular lip portion on the drum element which abuts against the rim or open end of the body member, the drum element having a diametrical passageway therethrough which interconnects the pair of arcuate metering grooves in the drum surface at their largest cross-sectional size ends. The drum element is provided with a diametrically slotted stud end projecting endwise therefrom and contractably insertable into and through a bore opening in the end wall of the chamber to cause an enlarged head end portion of the stud end to snap-lock behind the end wall of the chamber to secure the stem and body members together in assembled rotative relation.

According to yet another aspect of the invention, the actuating lever arm on the stem member of the device extends through the space defined by the sector-shaped frame on the body member so as to engage with the generally radially outward extending side support arms of the sector-shaped frame to limit the throw of the lever arm and angular extent of rotative movement of the stem member relative to the body member to that degree required to shift the stem member between a zero flow position and the maximum flow position thereof.

The principal object of the invention is to provide a liquid medium flow metering device of the type as referred to hereinabove which is of simple and easily fabricated inexpensive construction comprised of molded plastic body and stem members snap-locked together in rotative assembled relation.

Another object of the invention is to provide a liquid medium flow metering device as referred to above having body and stem members relatively rotatable to selected flow metering positions and provided with a retaining arrangement for maintaining the members in their set selected rotative flow metering position and affording a readily visible and easily recognizable indication of their set position.

Still another object of the invention is to provide a liquid medium flow metering device as referred to above having relatively rotatable stem and body members and provided with respective actuating arm means engageable with one another to limit the angular degree of relative rotative movement of the members.

A further object of the invention is to provide a liquid medium flow metering device as referred to above having body and stem members relatively rotatable to selected flow metering positions and wherein the rotative adjustment of the members to a precise setting within the minimum flow rate range of settings thereof is not a critical operation and can be easily effected.

A still further object of the invention is to provide a liquid medium flow metering device as referred to above having body and stem members relatively rotatable to selected flow metering positions and wherein the principal extent of metering of the liquid medium by the members occurs within around the first thirty degrees of relative rotative metering movement of the members following the start of their actual metering of the liquid medium flow rate from a zero flow rate.

Yet another object of the invention is to provide a liquid medium flow metering device as referred to above having body and stem members relatively rotatable to selected flow metering positions and having respective actuating arm means thereon for enabling the relative rotative metering movement of the members and providing retaining means for maintaining the members in their selected metering position.

Further objects and advantages of the invention will be apparent from the following detailed description of a preferred species thereof and from the accompanying drawings.

BRIEF DESCRIPTION OF THE INVENTION

Referring now to the drawings wherein the showings are for the purposes of illustrating a preferred embodiment of the invention only and not for the purpose of limiting same, the figures show the invention as embodied in a metering device or valve, particularly of the in-line type, for metering the flow of a liquid medium, e.g. a medical fluid, through a tubing system such as an intravascular catheter system. It is to be understood, however, that the invention may be utilized in fluid flow metering devices for use in various other tubing systems, whenever it may be found to have suitable utility therefor.

Figure 1:
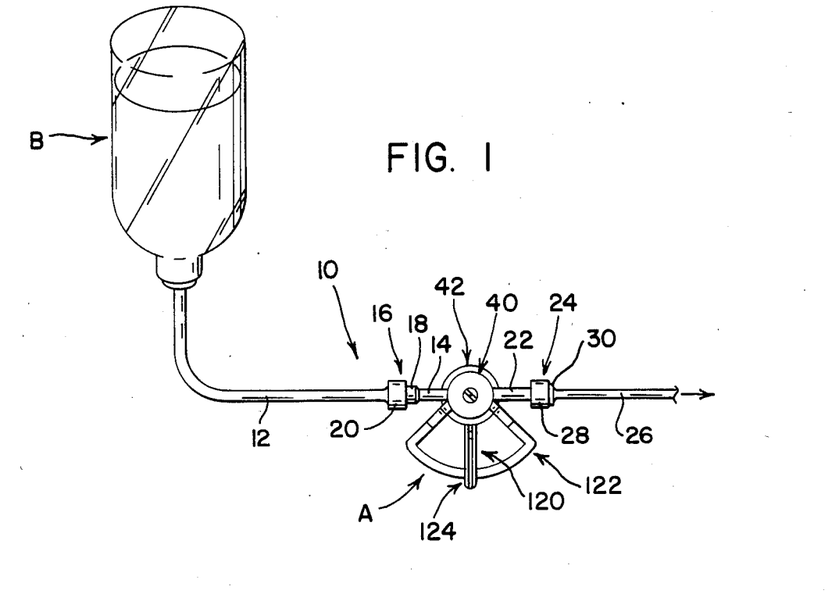
FIG. 1 is a schematic illustration of a portion of an intravascular catheter system provided with a metering device comprising the invention for metering the flow of medical fluid through the system.
Figure 2:
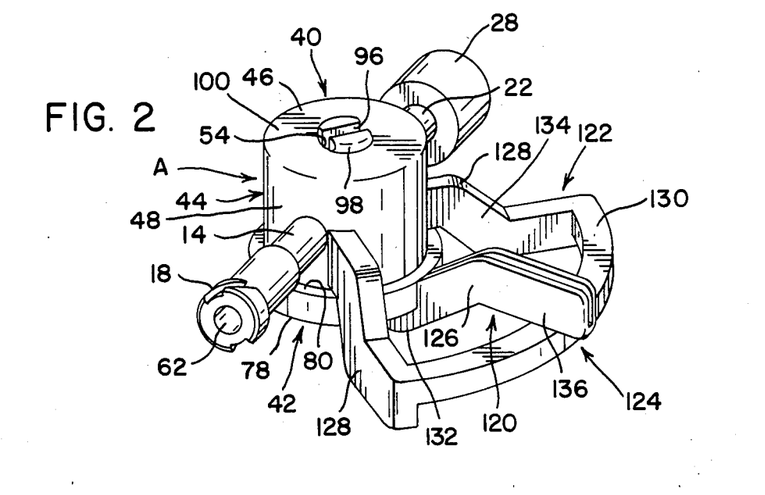
FIG. 2 is a perspective view on an enlarged scale of a metering device comprising the invention.

FIG. 1 illustrates a metering device or valve A according to the invention incorporated in an intravascular catheter system generally designated 10 and including a tubing section 12 of conventional Tygon tubing, for example, connecting a supply of a medical fluid such as a sterile saline solution in a container B to a short inlet connector tube or nipple 14 of the metering device A by a suitable coupling 16 such as a conventional Luer coupling comprising a male fitting 18 affixed to the free end of the inlet tube 14 and releaseably attached to a female fitting 20 attached to the end of tubing section 12. A short outlet tube or nipple 22 of the metering device A located in-line with the inlet nipple 14 thereof is releaseably attached by a similar coupling 24 to another tubing section 26 of the catheter system 10. Coupling 24 is comprised, as shown, of a female fitting 28 affixed to the free end of the outlet tube 22 and attached to a male fitting 30 affixed to an end of tubing section 26. In the operation of the catheter system 10, the metering device A thereof is adjusted to meter the flow of the medical fluid from container B in the necessary manner to provide the desired rate of outflow of the medical fluid, e.g. drops per unit time interval, through the tubing section 26 and through the catheter or other element (not shown) of the catheter system to which the tubing section 26 is connected.

The metering device or valve A according to the invention is comprised, in general, of an assembly of two separate molded plastic members, i.e. a body member 40 and a stem member 42 which are adapted to be snap-locked together in assembled rotative relation to each other. Body member 40 is comprised of a cup-shaped housing portion 44 having a flat end wall 46 and a cylindrical side wall portion 48 together defining a bore chamber 50 open at the one end 52 of housing portion 44 which is opposite the end wall 46 thereof. End wall 46 is provided with a centrally located circular bore opening 54 therethrough coaxial with the axis of the cylindrical bore wall surface 56 of bore chamber 50.

Diametrically opposite inlet and outlet port openings 58 and 60, respectively, opening into the chamber 50 are provided in the side wall 48 of the housing portion 44 of body member 40, at locations thereon more or less midway between the end wall 46 and the open outer end 52 of the body member, for the passage of a liquid medium into and out of the chamber. The housing portion 44 of body member 40 is provided with inlet and outlet tubular connector portions or nipples 14 and 22, respectively, as referred to previously, which extend radially outward from the cylindrical side wall 48 of the housing portion 44 in diametrically opposite in-line relation therefrom and in axial alignment with, and their internal passageways 62 and 64 in communication with the respective inlet and outlet port openings 58 and 60 in the chamber wall 48. Affixed to the free ends of the in-line tubular connector portions 14 and 22 are the male and female fittings 18 and 28 referred to previously, for attachment to the corresponding female and male fittings 20 and 30 affixed to the tubing sections 12 and 26.

The stem member 42 of the metering device A is comprised of a cylindrical drum element or portion 70 extending into and rotatively supported in the chamber 50 of the body member 40. Drum element 70 is preferably formed with a hollow interior and a cylindrical outer surface 72 rotatively engaged in liquid-tight relation with the cylindrical bore wall surface 56 of chamber 50 so as to rotatively support the stem member in the housing portion 44 of the body member 40 for relative rotative movement about the axis of the bore chamber 50. The stem member 42 is secured in assembled rotative relation with the body member 40 with the inner rim end 74 of the drum element 70 abutting endwise against the flat inner face 76 of the end wall 46 of the body member 40 and with an outward annular flange 78 on the outer end of the drum element overlapping and abutting against the outer rim end 52 of the body member. Flange 78 is formed therearound with a retroverted peripheral lip 80 having a cylindrical inner wall 82 concentric with and forming an annular groove 84 (FIG. 7) around the cylindrical outer surface 72 of the drum element 70. In the assembled position of the drum and stem members 40, 42, the outer rim end 52 of the side wall 48 of body member 40 fits into the groove 84, and the cylindrical inner wall 82 of the lip 80 on flange 78 rotatively engages around the cylindrical outer surface of the side wall 48, to thereby provide an additional rotative support of the stem member 42 on the body member 40.

The hollow cylindrical drum element 70 of the stem member 42 is provided more or less medially of its end 74 and its opposite end at flange 78 with an internal tubular portion 86 extending diametrically across the hollow interior of the drum element and having a bore passageway 88 therethrough which also extends diametrically across the drum element with its opposite ends 90, 92 opening at the cylindrical surface 72 of the drum element on diametrically opposite sides thereof. The open ends 90, 92 of the transverse bore passageway 88 are located at points along the length of the drum element 70 to register with the port openings 58 and 60, respectively, in the cylindrical side wall 48 of the housing portion 44 of body member 40 when the body and stem members 40, 42 are rotatively adjusted to their fully open position, as shown in FIG. 3.

The drum element 70 of the stem member 42 is provided with a diametrically slotted cylindrical stud end portion 94 projecting axially of the drum element from the internal tubular portion 86 thereof and endwise beyond its rim end 74. Stud end portion 94 extends into and through the bore opening 54 in end wall 46 of the housing portion 44 of body member 40 with a slight clearance therebetween and it is provided with a diametrical slot 96 and a rounded or tapered head end 98 of enlarged size, relative to the cylindrical portion of the stud end, in a direction normal to the slot 96. The provision of the diametrical slot 96 in the stud end portion 94 enables the spring contraction thereof into, and the passage of the stud end portion through the bore opening 54 in the body member 40 so that the enlarged head end 98 will snap out behind and engage with outer face 100 of the end wall 46 of the body member to thereby snap-lock the stem member 42 in assembled rotative relation with the body member, with the outward flange 78 on the drum element 70 held against the outer rim end 52 of the side wall 48 of body member 40 and with the inner rim end 74 of the drum element 70 held against the inner face 76 of the end wall 46 of body member 40.

Figure 3:
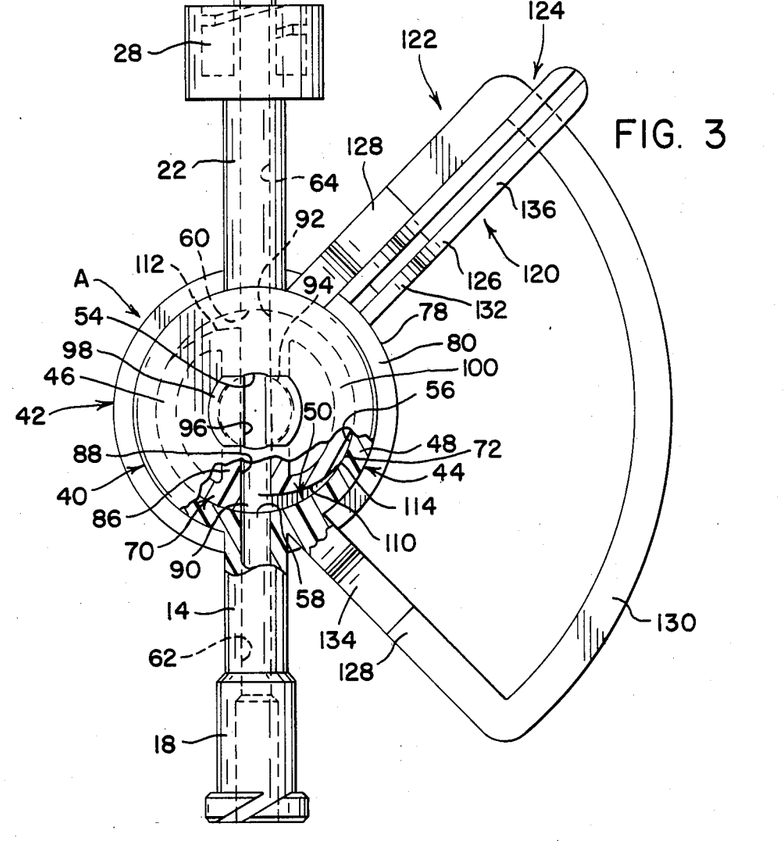
FIG. 3 is a plan view on an enlarged scale of the metering device comprising the invention showing the metering members thereof in their fully open position.
Figure 5:
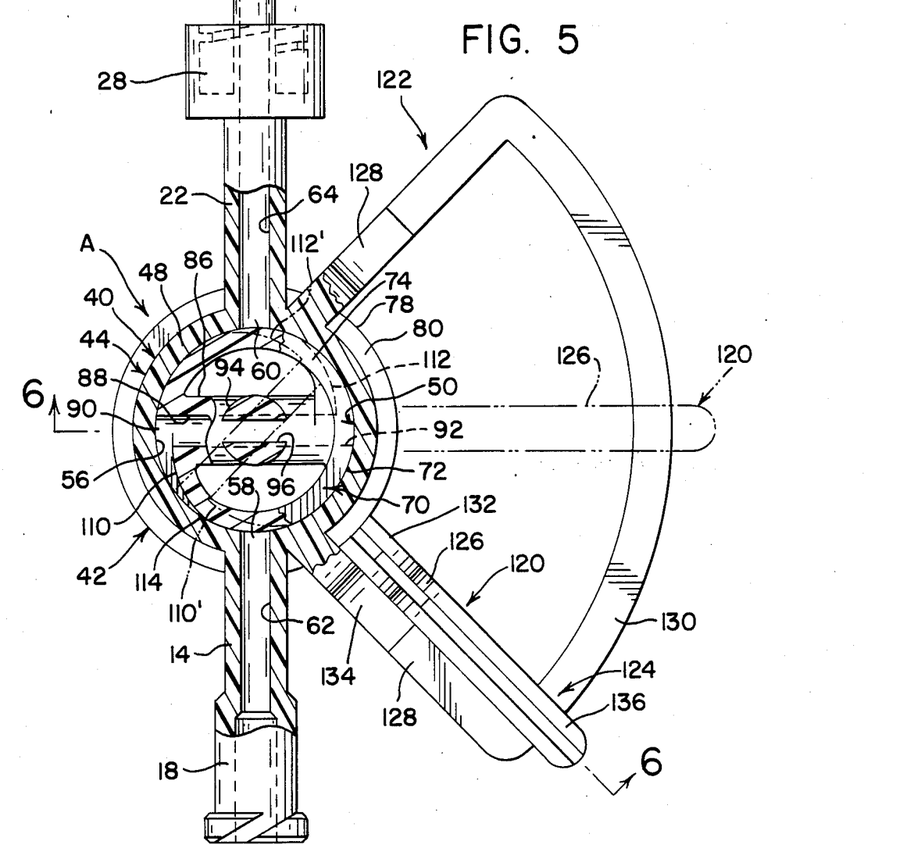
FIG. 5 is a plan view similar to FIG. 3 and partly in section but showing the metering members of the device in their fully closed position blocking the flow of fluid therethrough.
Figure 7:
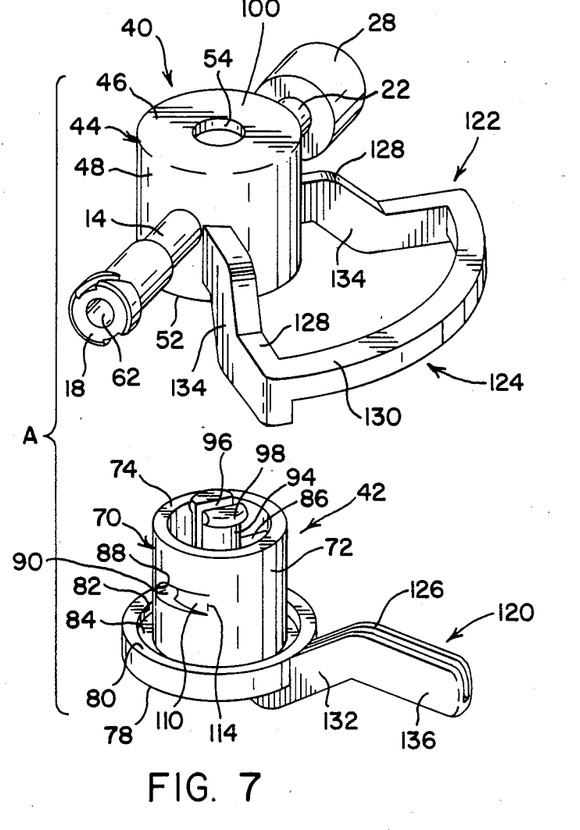
FIG. 7 is an exploded perspective view of the body and stem members of the device shown in position for assembly; and, FIG. 8 is a fragmentary elevation view of a modified form of retaining means for maintaining the body and stem members in a set metering position.

In accordance with the invention, the cylindrical outer surface 72 of the drum element 70 is provided with a pair of diametrically opposite, circumferentially extending, arcuate metering grooves 110 and 112 which open at one end into and communicate with respective ends 90, 92 of the transverse passageway 88 in the drum element and extend away therefrom in the same direction around the drum axis, i.e., counterclockwise as shown in FIGS. 3, 5 and 7. The metering grooves 110, 112 may be formed of any suitable cross-sectional shape such as U-shape or V-shape or semicircular-shape, but preferably are formed of square-sided cross-sectional shape with parallel side walls and a flat bottom face. The metering grooves 110, 112 each have an arcuate length around the drum surface 72, extending from the center axis of the transverse passageway 88, of around 60° or so and, as shown in FIGS. 3, 5 and 7, they are of spiral form with a progressively decreasing depth and therefore a progressively decreasing cross-sectional size or area leading away from the passageway 88 and merging into the cylindrical outer surface 72 of the drum element 70, as indicated at 114 in FIG. 7.

Figure 6:
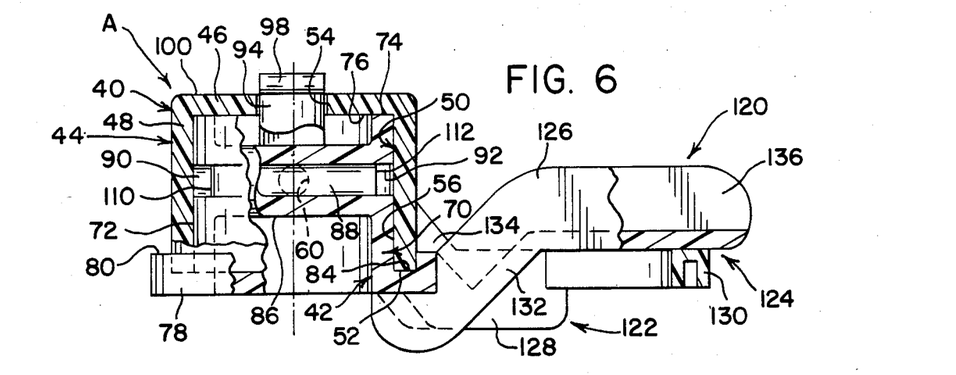
FIG. 6 is a sectional view on the line 6—6 of FIG. 5.

When the body and stem members 40 and 42 are in their closed relative rotative position as shown in FIGS. 5 and 6, the port openings 58, 60 of body member 40 are blocked off by the drum element 70 to prevent any flow of the liquid medium from container B through the inlet tube 14 and inlet port 58 into the chamber 50 of the metering device A and therethrough. However, when the members 40, 42 are relatively rotated to locate the metering grooves 110, 112 of the drum element 70 in any selected metering position thereof such as indicated in dash dot lines at 110', 112' in FIG. 5 where the grooves 110, 112 communicate with the port openings 58, 60, metered flow of the liquid medium is then produced from inlet tube 14 and inlet port 58 into and through inlet groove 110 and the communicating transverse passageway 88 and then through outlet groove 112 to the outlet port 60 and outlet tube 22. The rate of metered flow is, of course, dependent on the rotative metered positions of the body and stem members 40, 42 relative to one another and thus the relative angular position of inlet port 58 relative to the spiral inlet groove 110. Full unmetered flow of the liquid medium from container B through the metering device A is obtained when the members 40, 42 are rotated to their fully open position relative to one another as shown in FIG. 3 wherein the transverse passageway 88 in drum element 70 is aligned and registered with the port openings 58, 60, thus permitting full flow of the liquid medium from the inlet port 58 through the passageway 88 and out the outlet port 60 into the outlet tube 22.

In accordance with a preferred form of the invention, the spiral metering grooves 110, 112 are shaped so that the principal extent of metering of the liquid medium by the body and stem members 40, 42 occurs within around the first 30° or so of relative rotative metering movement of the members following the start of their actual metering of the liquid medium flow rate from a zero flow rate. To this end, the spiral metering grooves 110, 112 are preferably formed so that they extend more or less asymtotic to the cylindrical drum surface 72 in the direction of their mergence therewith at 114. As a result, the cross-sectional area of the spiral metering grooves 110, 112 decreases at a minimum rate toward their mergence with the drum surface 72, and the metering of the flow rate in turn varies minimally over an appreciable range of angular rotative movement of the members 40, 42 relative to one another within the minimum flow rate range of settings thereof. Accordingly, the precise setting of the members 40, 42 within such minimum flow rate range of settings is not particularly critical and thus can be easily effected. It should be noted that the mergence of the arcuate metering grooves 110, 112 with the cylindrical surface 72 of the drum element 70 at the points 114 thereon is so located therearound as to be spaced a sufficient angular distance around the cylindrical inner surface 56 of the bore chamber 50 from the port openings 58, 60 therein, when the members 40, 42 are in their inoperative position as shown in FIG. 5, to assure the complete covering and closing off of the port openings by the drum surface at such time.

The stem and body members 42 and 40 are provided with respective actuating arm means 120 and 122 for enabling convenient manual rotative adjustment of the members relative to one another to a selected metering position, and to also provide retaining means for maintaining the members 40, 42 in their selected rotative metering position. The actuating arm means 120 on the stem member 42 comprises a single lever arm 126 extending generally radially outward from the outward flange portion 78 and lip 80 of the stem member 42. Similarly, the actuating arm means 122 on the body member 40 comprises a pair of support arms 128 also extending generally radially outward from the body member on opposite sides of the lever arm 126 and angularly spaced apart around the body member a distance corresponding approximately to the extent of angular relative rotative movement of the members 40, 42 required to move them from their inoperative, fully closed position as shown in FIG. 5 to their fully open position as shown in FIG. 3. The pair of support arms 128 are interconnected at their outward ends by an arcuate bar portion 130 centered on the turning axis of the members 40, 42 and forming with the bar portion a sector-shaped frame extending outwardly from the body member.

Figure 4:
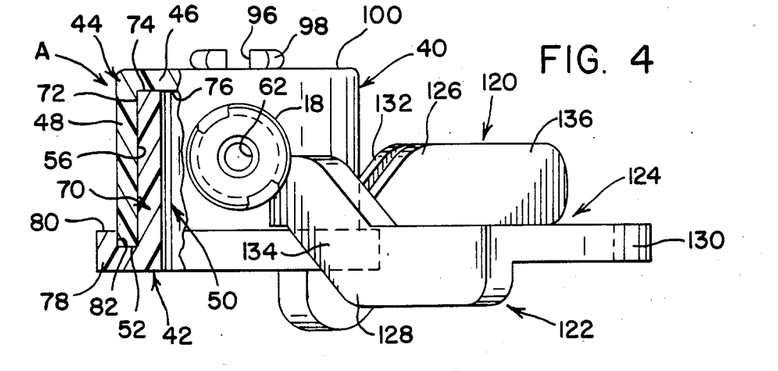
FIG. 4 is an elevation view on an enlarged scale and partly in section of the metering device shown in FIG. 3.

As shown best in FIGS. 4 and 6, at least one of the single lever arm 126 or the pair of support arms 128, and preferably both thereof as illustrated, is or are axially offset intermediate the ends thereof from one to the other axial side of the other of the lever arm 126 or the pair of support arms 128, as indicated at 132 and 134 respectively, so that the lever arm 126 extends through the space defined by the sector-shaped frame 128, 130 and is engageable with the support arms 128 thereof to limit the throw of the lever arm and the angular extent of rotative movement of the stem member 42 relative to the body member 40 to that required to adjust these members from their closed position (FIG. 5) to their fully open position (FIG. 3). In the assembled position of the body and stem members 40, 42, the offset outer end portion 136 of the lever arm 126 extends radially across and is slightly deflected axially of the turning axis of the members 40, 42 so as to have a slight degree of spring pressure against and thus frictional sliding engagement with the arcuate bar portion 130 which thus functions somewhat as a retaining means 124 for frictionally holding the body and stem members 40, 42 in their selected or set rotative metering position. Preferably, however, the lever arm 126 and arcuate bar portion 130 are provided with a ratcheting arrangement 140 as shown in FIG. 8 for positively locking the body and stem members 40, 42 in their set rotative metering position against accidental displacement therefrom.

Figure 8:
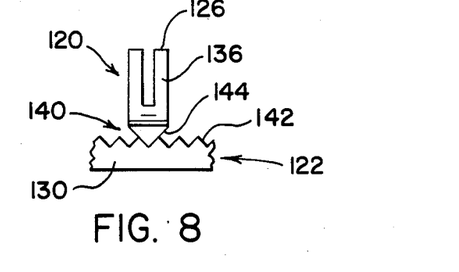

Referring to FIG. 8, the ratcheting arrangement 140 is comprised of a series of relatively small V-section ratchet teeth 142 provided on that face of the arcuate bar portion 130 which is engaged by the offset outer end 136 of the lever arm 126, and a detent 144 of corresponding V-section on the outer end of the lever arm and engaging with the ratchet teeth 142 to lock the lever arm in place in the set metering position along the bar against accidental displacement therealong, thus providing a positive locking arrangement for maintaining the members 40, 42 in their set metering position. Such a ratcheting arrangement 140 enables easy rotative movement of the members 40, 42 in either relative rotative direction due to the camming action of the engaged V-section ratchet teeth 142 and detent 144 to provide self-disengagement therebetween. This is of particular advantage during the rotative adjustment of the members 40, 42 relative to one another to achieve the desired selected metering setting thereof.

The body and stem members 40, 42 are molded of a suitable synthetic plastic material such as forms a soft, pliable, end product. Accordingly, in fitting the body and stem members 40, 42 together to form the completed metering device assembly A, the pliable character of the actuating arm means 120, 122 permits the flexure thereof axially of the turning axis of the members 40, 42 to the necessary degree, after first passing the lever arm 126 through the space enclosed by the sector-shaped frame 128, 130, to enable the axial alignment of the cylindrical drum element 70 with the cylindrical chamber 50 of the body member 40 for insertion thereinto. On continued insertion movement of the inserted drum element 70 into the chamber 50, the projecting slotted stud end portion 94 of the drum element is then contracted, by the camming action of its rounded head end 98 against the peripheral edge of the bore opening 54 in the end wall 46 of the body member 40, to permit the passage of the stud end portion and its enlarged head end 98 into and through the bore opening 54. When the drum element 70 is fully inserted in place in the chamber 50, with its inner rim end 74 abutting against the inner face 76 of the end wall 46 of body member 40, the head end 98 of the contracted stud end portion 94 is then clear of and free to snap outwardly over and behind the outer face 100 of the end wall 46 of the base member, thus snap-locking the stem and bore members 42, 40 together in their assembled position. On completion of this assembly operation, the actuating arm means 120 and 122 which necessarily must be spring flexed relative to one another axially of the turning axis of the members 40, 42 in order to permit the axial alignment of the drum element 70 with the chamber 50 for insertion thereinto, remain in a slightly spring flexed relative position. As a result, the lever arm 126 is in spring pressed sliding frictional engagement with the arcuate bar portion 130 of the actuating arm means 122 to thereby provide the retaining means 124 for maintaining the members 40, 42 in their set rotative metering position.

It will be evident that the particular actuating arm means 120, 122 according to the invention for adjusting the rotative setting of the members 40, 42 provides a readily visible and easily recognizable indication of the setting of the device A for a particular metered flow rate of the liquid medium from the device. This is of especial advantage for certain purposes as, for instance, where repeated checking of the setting of the device A is made to determine whether or not the original metered setting thereof has been accidentally altered, or where the metering device is moved to a closed position for some reason or other, for instance, to check the reason for a stoppage of the liquid flow through the tubing system and the metering device is to be restored to the previous metered setting thereof. Also, the asymtotic mergence of the spiral metering grooves 110, 112 in the drum element 70 with the cylindrical outer surface 72 thereof affords a relatively wide range of angular adjustment movement of the stem member 42 relative to the body member 40, e.g., 30° or so of such angular adjustment movement, within the minimum flow rate range of adjustment settings of these members. As a consequence, the setting of the members 40, 42 within such minimum flow rate range of settings to provide a precise minimal flow rate, e.g., a prescribed small number of drops per minute of the liquid medium, is not a critical operation to perform but instead can be easily and quickly accomplished.

Having thus described the invention, it is claimed:

1. An in-line metering device for regulating the flow of a liquid medium therethrough, said device comprising a one-piece molded plastic body member of cup-shaped form and comprised of cylindrical side wall and an end closure wall integral therewith and extending transversely across and closing one end of said cylindrical side wall to define therewith a bore chamber open at the end opposite said end closure wall, said cylindrical side wall being provided with a pair of diametrically opposite port openings therein opening into said chamber, a stem member comprising a cylindrical drum element extending into and rotatively engaged in liquid tight relation with the cylindrical bore wall of said bore chamber, said drum element having a stud end portion projecting endwise therefrom through a bore opening in said end closure wall and snap-locked in place thereon to secure the said members together in rotative assembled relation with the said drum element abutting endwise against and engaging around its inner rim end with the said end closure wall, said drum element having a diametrical passageway extending transversely therethrough for registering with and interconnecting said port openings in the fully open rotative metering position of said members relative to one another, and said drum element being provided with a pair of diametrically opposite arcuate metering grooves in the cylindrical outer surface thereof, said grooves communicating at one end with respective ends of said passageway and extending therefrom in the same circumferential direction around the drum element, said grooves being of corresponding spiral-like form characterized by a progressively decreasing cross-sectional area leading away from said passageway and merging flush with the cylindrical surface of said drum element.

2. A metering device as defined in claim 1, wherein the said arcuate metering grooves have corresponding arcuate extends of less than 90° such that the said grooves are completely out of registry with said port openings when the said members are rotated to their closed relative position with the said diametrical passageway extending transversely to the common axis of said diametrically opposite port openings.

3. A metering device as defined in claim 1, wherein an appreciable portion of the arcuate length of the said metering grooves extending from their mergence with the cylindrical surface of said drum element extends asymtotic to the said drum surface.

4. A metering device as defined in claim 3, wherein the said asymtotic portions of said arcuate metering grooves have an arcuate extent of around 30° each.

5. A metering device as defined in claim 3, wherein the said arcuate metering grooves have corresponding total arcuate extents of around 60° each.

6. An in-line metering device for regulating the flow of a liquid medium therethrough, said device comprising a cup-shaped body member having an end closure wall and a surrounding side wall defining therewith a bore chamber open at the end opposite said end closure wall, the said end closure wall extending inwardly from said side wall across the said bore chamber at one end thereof and said side wall being provided with a pair of diametrically opposite port openings therein opening into said chamber, a stem member comprising a cylindrical drum element extending into and rotatively engaged in liquid tight relation with the cylindrical bore wall of said chamber, a stud end portion projecting endwise from said drum element through a bore opening in said end closure wall and snap-locked in place thereon to secure the said members together in rotative assembled relation with the said drum element abutting endwise against the said end closure wall, the said projecting stud end portion of said drum element being diametrically slotted to permit the spring contraction thereof to a smaller diametrical dimension across one of its diameters for insertion through the said bore opening in said end wall, and said projecting stud end portion being provided around its outermost end with laterally outward extending locking lip means of cam-shaped section for engaging with the wall of said bore opening to contract the said slotted stud end portion for insertion into and passage through said bore opening to snap-lock behind said end wall, said drum element having a diametrical passageway extending transversely therethrough for registering with and interconnecting said port openings in the fully open rotative metering position of said members relative to one another, and said drum element being provided with a pair of dimetrically opposite arcuate metering grooves in the cylindrical outer surface thereof, said grooves communicating at one end with respective ends of said passageway and extending therefrom in the same circumferential direction around the drum element, said grooves being of corresponding spiral-like form characterized by a progressively decreasing cross-sectional area leading away from said passageway and merging flush with the cylindrical surface of said drum element.

7. A metering device as defined in claim 6, wherein an appreciable portion of the arcuate length of the said metering grooves extending from their mergence with the cylindrical surface of said drum element extends asymtotic to the said drum surface.

8. A metering device as defined in claim 7, wherein the said asymtotic portions of the said arcuate metering grooves have an arcuate extent of around 30° each.

9. A metering device as defined in claim 7, wherein the said arcuate metering grooves have corresponding total arcuate extents of around 60° each.

10. A metering device as defined in claim 1, wherein the said body member is provided with diametrically opposite outwardly projecting in-line tubular connector portions with internal passages therethrough communicating with respective ones of the said port openings in said body member, said tubular connector portions being provided at their outward ends with fittings for coupling said connector portions to respective tubing sections of a tubing system.

11. A metering device for regulating the flow of a liquid medium therethrough, said device comprising a cup-shaped body member having an end closure wall and a surrounding side wall defining therewith a bore chamber open at the end opposite said end closure wall, the said end closure wall extending inwardly from said side wall across the said bore chamber at one end thereof and said side wall being provided with a pair of diametrically opposite port openings therein opening into said chamber, a stem member comprising a cylindrical drum element extending into and rotatively engaged in liquid tight relation with the cylindrical bore wall of said chamber, a stud end portion projecting endwise from said drum element through a bore opening in said end closure wall and snap-locked in place thereon to secure the said members together in rotative assembled relation with the said drum element abutting endwise against the said end closure wall, the outer surface of the said side wall of said body member being of cylindrical form coaxial with the said bore chamber threrof, and the said drum element being provided at its outer end with a laterally outward projecting annular flange abutting against the outer rim end of the body member and formed with a retroverted peripheral lip with a cylindrical inner wall concentric with and rotativebly engaged with the said cylindrical outer surface of the said side wall of said body member to further rotatively support the said stem member on said body member, said drum element having a diametrical passageway extending transversely therethrough for registering with and interconnecting said port openings in the fully open rotative metering position of said members relative to one another, and said drum element being provided with a pair of diametrically opposite arcuate metering grooves in the cylindrical outer surface thereof, said grooves communicating at one end with respective ends of said passageway and extending therefrom in the same circumferential direction around the drum element, said grooves being of corresponding spiral-like form characterized by a progressively decreasing cross-sectional area leading away from said passageway and merging flush with the cylindrical surface of said drum element.

12. A metering device as defined in claim 1, wherein the said body and stem members are provided with respective actuating arm means extending generally radially outward from the said members.

13. A metering device as defined in claim 3, wherein the said body and stem members are provided with respective actuating arm means extending generally radially outward from the said members.

14. A metering device as defined in claim 4, wherein the said body and stem members are provided with respective actuating arm means extending generally radially outward from the said members.

15. A metering device as defined in claim 6, wherein the said body and stem members are provided with respective actuating arm means extending generally radially outward from the said members.

16. An in-line metering device for regulating the flow of a liquid medium therethrough, said device comprising a cup-shaped body member having an end closure wall and a surrounding side wall defining therewith a bore chamber open at the end opposite said end closure wall, the said end closure wall extending inwardly from said side wall across the said bore chamber at one end thereof and said side wall being provided with a pair of diametrically opposite port openings therein opening into said chamber, a stem member comprising a cylindrical drum element extending into and rotatively engaged in liquid tight relation with the cylindrical bore wall of said chamber, a stud end portion projecting endwise from said drum element through a bore opening in said end closure wall and snap-locked in place thereon to secure the said members together in rotative assembled relation with the said drum element abutting endwise against the said end closure wall, said drum element having a diametrical passageway extending transversly therethrough for registering with and interconnecting said port openings in the fully open rotative metering position of said members relative to one another, and said drum element being provided with a pair of diametrically opposite arcuate metering grooves in the cylindrical outer surface thereof, said grooves communicating at one end with respective ends of said passageway and extending therefrom in the same circumferential direction around the drum element, said grooves being of corresponding spiral-like form characterized by a progressively decreasing cross-sectional area leading away from said passageway and merging flush with the cylindrical surface of said drum element, and the said body and stem members being provided with respective actuating arm means extending generally radially outward from the said members, the said acutating arm means having respective portions thereof in spring pressed sliding interengagement, during relative rotation of said members, to provide retaining means for maintaining said members in a selected rotative metering position relative to one another.

17. An in-line metering device for regulating the flow of a liquid medium therethrough, said device comprising a cup-shaped body member having an end closure wall and a surrounding side wall defining therewith a bore chamber open at the end opposite said end closure wall, the said end closure wall extending inwardly from said side wall across the said bore chamber at one end thereof and said side wall being provided with a pair of diametrically opposite port openings therein opening into said chamber, a stem member comprising a cylindrical drum element extending into and rotatively engaged in liquid tight relation with the cylindrical bore wall of said chamber, a stud end portion projecting endwise from said drum element through a bore opening in said end closure wall and snap-locked in place thereon to secure the said members together in rotative assembled relation with the said drum element abutting endwise against the said end closure wall, said drum element having a diametrical passageway extending transversely therethrough for registering with and interconnecting said port openings in the fully open rotative metering position of said members relative to one another, and said drum element being provided with a pair of diametrically opposite arcuate metering grooves in the cylindical outer surface thereof, said grooves communicating at one end with respective ends of said passageway and extending therefrom in the same circumferential direction around the drum element, said grooves being of corresponding spiral-like form characterized by a progressively decreasing cross-sectional area leading away form said passageway and merging flush with the cylindrical surface of said drum element, an appreciable portion of the arcuate length of the said metering grooves extending from their mergence with the cylindrical surface of said drum element extending asymptotic to the said drum surface, and the said body and stem members being provided with respective actuating arm means extending generally radially outward from the said members, the said actuating arm means having respective portions thereof in spring pressed sliding interengagement, during relative rotation of said members, to provide retaining means for maintaining said members in a selected rotative metering position relative to one another.

18. An in-line metering device for regulating the flow of a liquid medium therethrough, said device comprising a cup-shaped body member having an end closure wall and a surrounding side wall defining therewith a bore chamber open at the end opposite said end closure wall, the said end closure wall extending inwardly form said side wall across the said bore chamber at one end thereof and said side wall being provided with a pair of diametrically opposite port openings therein opening into said chamber, a stem member comprising a cylindrical drum element extending into and rotatively engaged in liquid tight relation with the cylindrical bore wall of said chamber, a stud end portion projecting endwise from said drum element through a bore opening in said end closure wall and snap-locked in place thereon to secure the said members together in rotative assembled relation with the said drum element abutting endwise against the said end closure wall, said drum element having a diametrical passageway extending transversely therethrough for registering with and interconnecting said port openings in the fully open rotative metering position of said members relative to one another, and said drum element being provided with a pair of diametrically opposite arcuate metering grooves in the cylindrical outer surface thereof, said grooves communicating at one end with respective ends of said passageway and extending therefrom in the same circumferential direction around the drum element, said grooves being of corresponding spiral-like form characterized by a progressively decreasing cross-sectional area leading away from said passageway and merging flush with the cylindrical surface of said drum element, an appreciable portion of the arcuate length of the said metering grooves extending from their mergence with the cylindircal surface of said drum element extending asymptotic to the said drum surface, the said asmptotic portions of said arcuate metering grooves having an arcuate extent of around 30° each, and the said body and stem members being provided with respective acutating arm means extending generally radially outward from the said members, the said actuating arm means having respective portions thereof in spring pressed sliding interengagement, during relative rotation of said members, to provide retaining means for maintaining said members in a selected rotative metering position relative to one another.

19. An in-line metering device for regulating the flow of a liquid medium therethrough, said device comprising a cup-shaped body member having an end closure wall and a surrounding side wall defining therewith a bore chamber open at the end opposite said end closure wall, the said end closure wall extending inwardly from said side wall across the said bore chamber at one end thereof and said side wall being provided with a pair of diametrically opposite port openings therein opening into said chamber, a stem member comprising a cylindrical drum element extending into and rotatively engaged in liquid tight relation with the cylindrical bore wall of said chamber, a stud end portion projecting endwise from said drum element through a bore opening in said end closure wall and snap-locked in place thereon to secure the said members together in rotative assembled relation with the said drum element abutting endwise against the said end closure wall, the said projecting stud end portion of said drum element being diametrically slotted to permit the spring contraction thereof to a smaller diametrical dimension across one of its diameters for insertion through the said bore opening in said end wall, and said projecting stud end portion being provided around its outermost end with laterally outward extending locking lip means of cam-shaped section for engaging with the wall of said bore opening to contract the said slotted stud end portion for insertion into and passage through said bore opening to snap-lock behind said end wall, said drum element having a diametrical passageway extending transversely therethrough for registering with and interconnecting said port openings in the fully open rotative metering position of said members relative to one another, and said drum element being provided with a pair of diametrically opposite arcuate metering grooves in the cylindrical outer surface thereof, said grooves communicating at one end with respective ends of said passageway and extending therefrom in the same circumferential direction around the drum element, said grooves being of corresponding spiral-like form characterized by a progressively decreasing cross-sectional area leading away from said passageway and merging flush with the cylindrical surface of said drum element, and the said body and stem members being provided with respective actuating arm means extending generally radially outward from the said members, the said actuating arm means having respective portions thereof in spring pressed sliding interengagement, during relative rotation of said members, to provide retaining means for maintaining said members in a selected rotative metering position relative to one another.

20. An in-line metering device for regulating the flow of a liquid medium therethrough, said device comprising a cup-shaped body member having an end wall and a surrounding side wall defining therewith a bore chamber open at the end opposite said end wall, said side wall being provided with a pair of diametrically opposite port openings therein opening into said chamber, a stem member comprising a cylindrical drum element extending into and rotatively engaged in liquid tight relation with the cylindrical bore wall of said chamber, a stud end portion projecting endwise from said drum element through a bore opening in said end wall and snap-locked in place thereon to secure the said members together in rotative assembled relation, said drum element having a diametrical passageway extending transversely therethrough for registering with and interconnecting said port openings in the fully open rotative metering position of said members relative to one another, said drum element being provided with a pair of diametrically opposite arcuate metering grooves in the cylindrical surface thereof, said grooves communicating at one end with respective ends of said passageway and extending therefrom in the same direction around the drum element, said grooves being of corresponding spiral form characterized by a progressively decreasing cross-sectional area leading away from said passageway and merging flush with the cylindrical surface of said drum element, said body and stem members being provided with respective actuating arm means extending generally radially outward from the said members, the said actuating arm means on one of said members comprising a pair of support arms angularly spaced apart around the turning axis of said members and interconnected at their outward ends by an arcuate bar portion concentric with the said turning axis and forming with said support arms a sector-shaped frame on said one member, and the said actuating arm means on the other one of said members comprising a single lever arm extending between said support arms through the space defined by said frame and radially across and in spring pressed sliding engagement with the said arcuate bar portion to provide retaining means for maintaining the said members in a selected rotative metering position relative to one another.

21. A metering device as defined in claim 20, wherein the said pair of support arms extend outward from, and the said frame is supported on said body member, and the said single lever arm extends outward from the said stem member.

22. A metering device as defined in claim 20, wherein at least one of either said single lever arm or said pair of support arms is axially offset intermediate the ends thereof from one to the other axial side of the other one of said single lever arm or said pair of support arms.

23. A metering device as defined in claim 20, wherein the said single lever arm is engageable with the said support arms to limit the extent of rotative movement of said members relative to one another.

24. A metering device as defined in claim 22, wherein each said single lever arm and said pair of support arms is axially offset intermediate their respective ends from one to the other axial side of the other of said single lever arm and said pair of support arms.

25. A metering device as defined in claim 20, wherein the said arcuate bar portion comprises a ratchet bar and the said single lever arm is provided with detent means in ratcheting engagement with said ratchet bar to form the said retaining means.

26. A metering device as defined in claim 25, wherein the said pair of support arms extend outward from, and the said frame is supported on said body member, and the said single lever arm extends outwardly from the said stem member.

27. A metering device as defined in claim 25, wherein at least one of either said single lever arm or said pair of support arms is axially offset intermediate the ends thereof from one to the other axial side of the other one of said single lever arm or said pair of support arms.

28. A metering device as defined in claim 25, wherein each said single lever arm and said pair of support arms is axially offset intermediate their respective ends from one to the other axial side of the other of said single lever arm and said pair of support arms.

29. A metering device as defined in claim 20, wherein the said body and stem members are formed of pliable molded plastic material.

* * * * *